United States Patent
Alexander et al.

(10) Patent No.: US 9,510,825 B2
(45) Date of Patent: Dec. 6, 2016

(54) TOOLS AND METHODS FOR TREATMENT OF PELVIC CONDITIONS

(75) Inventors: James A. Alexander, Excelsior, MN (US); Chaouki A. Khamis, Edina, MN (US); Patricia M. Derus, Rogers, MN (US); Scott S. Jeutter, Richfield, MN (US); Gary A. Rocheleau, Maple Grove, MN (US); Steven G. Rockow, Coon Rapids, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 396 days.

(21) Appl. No.: 14/115,239

(22) PCT Filed: May 4, 2012

(86) PCT No.: PCT/US2012/036633
§ 371 (c)(1),
(2), (4) Date: Dec. 5, 2013

(87) PCT Pub. No.: WO2012/151543
PCT Pub. Date: Nov. 8, 2012

(65) Prior Publication Data
US 2014/0088349 A1      Mar. 27, 2014

Related U.S. Application Data

(60) Provisional application No. 61/482,911, filed on May 5, 2011.

(51) Int. Cl.
*A61B 17/064* (2006.01)
*A61F 2/00* (2006.01)
(Continued)

(52) U.S. Cl.
CPC ......... *A61B 17/0642* (2013.01); *A61B 17/064* (2013.01); *A61B 17/068* (2013.01);
(Continued)

(58) Field of Classification Search
CPC ............ A61B 17/064; A61B 17/0642; A61B 17/068; A61B 2017/00805; A61B 2017/0647; A61B 2017/0649; A61B 2017/00398; A61B 2017/00424; A61B 2017/2911; A61B 2017/2913; A61F 2/0045; A61F 2/0063
See application file for complete search history.

(56) References Cited

U.S. PATENT DOCUMENTS

| 3,580,313 A | 5/1971 | McKnight |
|---|---|---|
| 4,848,341 A | 7/1989 | Ahmad |

(Continued)

FOREIGN PATENT DOCUMENTS

| WO | WO 97/30638 A1 | 8/1997 |
|---|---|---|
| WO | 97/32527 A1 | 9/1997 |

(Continued)

OTHER PUBLICATIONS

Benderev, Theodore, "Anchor Fixation and Other Modifications of Endoscopic Bladder Neck Suspension," Urology, vol. 40, No. 5, Nov. 1992, pp. 409-419.

(Continued)

*Primary Examiner* — Christine H Matthews
*Assistant Examiner* — Joshua D Lannu
(74) *Attorney, Agent, or Firm* — Kagan Binder, PLLC

(57) ABSTRACT

A tool for driving a helical anchor into a target location, the tool including a proximal portion and a distal portion, the proximal portion having a handle and an actuator, and a shaft extending distally from the proximal portion, the shaft comprising an outer shaft and an inner rotating shaft that is at least partially concentrically positioned within the outer shaft, the shaft having a length that facilitates accessing a location of a posterior pelvic region, wherein the inner rotating shaft is actuated by movement of the actuator in a predetermined motion.

20 Claims, 12 Drawing Sheets

(51) Int. Cl.
*A61B 17/068* (2006.01)
*A61B 17/00* (2006.01)
*A61B 17/29* (2006.01)

(52) U.S. Cl.
CPC ........... *A61F 2/0045* (2013.01); *A61F 2/0063* (2013.01); *A61B 2017/00398* (2013.01); *A61B 2017/00424* (2013.01); *A61B 2017/00805* (2013.01); *A61B 2017/0647* (2013.01); *A61B 2017/0649* (2013.01); *A61B 2017/2911* (2013.01); *A61B 2017/2913* (2013.01)

(56) References Cited

U.S. PATENT DOCUMENTS

| | | | |
|---|---|---|---|
| 5,085,661 | A | 2/1992 | Moss |
| 5,824,008 | A * | 10/1998 | Bolduc ............... A61B 17/064 227/901 |
| 5,830,221 | A | 11/1998 | Stein et al. |
| 5,830,231 | A * | 11/1998 | Geiges, Jr. ......... A61B 17/2909 606/1 |
| 6,099,538 | A | 8/2000 | Moses |
| 6,328,744 | B1 | 12/2001 | Harari et al. |
| 6,612,977 | B2 | 9/2003 | Staskin et al. |
| 6,648,921 | B2 | 11/2003 | Anderson et al. |
| 6,691,711 | B2 | 2/2004 | Raz et al. |
| 6,974,462 | B2 | 12/2005 | Sater |
| 7,025,063 | B2 | 4/2006 | Snitkin et al. |
| 7,070,556 | B2 | 7/2006 | Anderson et al. |
| 7,189,251 | B2 * | 3/2007 | Kay ................... A61B 17/0401 411/395 |
| 7,303,525 | B2 | 12/2007 | Watschke et al. |
| 7,347,812 | B2 | 3/2008 | Mellier |
| 7,351,197 | B2 | 4/2008 | Montpetit et al. |
| 7,407,480 | B2 | 8/2008 | Staskin et al. |
| 7,422,557 | B2 | 9/2008 | Arnal et al. |
| 7,500,945 | B2 | 3/2009 | Cox et al. |
| 7,722,528 | B2 | 5/2010 | Arnal et al. |
| 7,740,576 | B2 | 6/2010 | Hodroff et al. |
| 7,901,346 | B2 | 3/2011 | Kovac et al. |
| 7,905,825 | B2 | 3/2011 | Arnal et al. |
| 7,914,437 | B2 | 3/2011 | Gozzi et al. |
| 2002/0028980 | A1 | 3/2002 | Thierfelder et al. |
| 2002/0147382 | A1 | 10/2002 | Neisz et al. |
| 2002/0151762 | A1 | 10/2002 | Rocheleau et al. |
| 2004/0193217 | A1 | 9/2004 | Lubbers et al. |
| 2005/0222665 | A1 | 10/2005 | Aranyi |
| 2006/0069301 | A1 | 3/2006 | Neisz et al. |
| 2006/0129154 | A1 | 6/2006 | Shipp |
| 2006/0195007 | A1 | 8/2006 | Anderson et al. |
| 2006/0195010 | A1 | 8/2006 | Arnal et al. |
| 2006/0195011 | A1 | 8/2006 | Arnal et al. |
| 2008/0132754 | A1 | 6/2008 | Thierfelder et al. |
| 2008/0207988 | A1 | 8/2008 | Hanes |
| 2009/0188965 | A1 | 7/2009 | Levin et al. |
| 2010/0174134 | A1 | 7/2010 | Anderson et al. |
| 2010/0256442 | A1 | 10/2010 | Ogdahl et al. |
| 2010/0280309 | A1 * | 11/2010 | von Pechmann ... A61B 17/00234 600/37 |
| 2010/0298630 | A1 | 11/2010 | Wignall |
| 2012/0160896 | A1 | 6/2012 | Houard |

FOREIGN PATENT DOCUMENTS

| | | |
|---|---|---|
| WO | WO 2007/016083 | 2/2007 |
| WO | WO 2007/097994 | 8/2007 |
| WO | WO 2007/149348 | 12/2007 |
| WO | WO 2008/057261 | 5/2008 |
| WO | WO 2009/017680 | 2/2009 |
| WO | WO 2010/093421 | 8/2010 |
| WO | 2011/015789 A1 | 2/2011 |
| WO | WO 2011/082350 | 7/2011 |

OTHER PUBLICATIONS

Laparoscopic Sacral Colpopexy. Procedure [online]. Mikos and Moore. Dec. 18, 2010. [retrieved on Aug. 12, 2012]. Retrieved from the Internet:<URL: web.archive.org/web/20101218101256/http://mikiosandmoore.com/lap_proc8a.php>. pp. 2-3.

* cited by examiner

TOOLS AND METHODS FOR TREATMENT OF PELVIC CONDITIONS

CROSS REFERENCE TO RELATED APPLICATION

This application claims the benefit from International No. PCT/US2012/036633, which was granted an International filing date of May 4, 2012, which in turns claims priority under 35 U.S.C. §119(e) of U.S. Provisional Patent Application No. 61/482,911, filed May 5, 2011 and titled "Tools and Methods for Treatment of Pelvic Conditions", which application are incorporated herein by reference in its entirety.

FIELD OF THE INVENTION

The present invention relates to tools and related methods for treating pelvic conditions by use of a pelvic implant to support pelvic tissue. The pelvic treatments can include, for example, treatment of vaginal prolapse by laparoscopic, abdominal, and transvaginal procedures.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions that affect the pelvic floor. Pelvic disorders such as these can result from weakness or damage to normal pelvic support systems. Common etiologies include childbearing, removal of the uterus, connective tissue defects, prolonged heavy physical labor and postmenopausal atrophy.

In more particularity, pelvic floor disorders include cystocele, rectocele, and prolapse such as anal, uterine, and vaginal vault prolapse. Vaginal vault prolapse is a condition that occurs when the upper portion of the vagina loses its normal shape and moves downwardly into the vaginal canal. In its severest forms, vaginal vault prolapse can result in the distension of the vaginal apex outside of the vagina. Vaginal vault prolapse may occur alone, such as can be caused by weakness of the pelvic and vaginal tissues and muscles, or can be associated with a rectocele, cystocele and/or enterocele. A rectocele is caused by a weakening or stretching of tissues and muscles that hold the rectum in place, which can result in the rectum moving from its usual location to a position where it presses against the back wall of the vagina. A cystocele is a hernia of the bladder, usually into the vagina and introitus. An enterocele is a vaginal hernia in which the peritoneal sac containing a portion of the small bowel extends into the rectovaginal space. All of these conditions can represent challenging forms of pelvic disorders for surgeons to treat, which treatment procedures can involve relatively lengthy surgical procedure times. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair vaginal vault prolapse by suturing the vaginal vault (e.g., by stitches) to the supraspinous ligament or by attaching the vaginal vault through mesh or fascia to the sacrum.

There is ongoing need in obtaining improved, e.g., minimally invasive, safe, and highly effective, methods for treating pelvic conditions including incontinence, vaginal prolapse (e.g., vaginal vault prolapse), and other pelvic organ prolapse conditions.

SUMMARY

Tools, systems, and methods as described herein can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies, and the like. In accordance with the invention, sacral colpopexy installation procedures can be performed through an abdominal opening, laparoscopically, or transvaginally, which procedures will require different approaches, each of which can use certain embodiments of devices and methods of the invention In a sacral colpopexy procedure it is desirable to simplify the procedure so the surgeon is not overwhelmed. One aspect of certain sacral colpopexy procedures is to place a fixation element (anchor such as a bone anchor or soft tissue anchor) into tissue of a posterior pelvic region, to secure an implant to the tissue. This aspect of the procedure requires a surgeon to place a tissue anchor at a location deep inside of a posterior pelvic region. The working space is small, as is the fixation element, and proper placement is important to safety and effectiveness of the surgery. Devices described herein provide methods for placing a fixation element (e.g., a helical anchor) by methods that improve safety, simplicity, and certainty. Useful features of these drivers include, for example, an elongate shaft that can reach a posterior pelvic region to place a helical anchor; optionally the ability to operate the tool with one hand; and generally improved control of placement, location, and depth of a helical anchor.

Certain embodiments relate generally to fixation or attachment devices ("anchors") and related methods for placing a pelvic mesh implant, and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include a tissue support portion and one or more anchors, arms and the like. In addition, disclosed are combination devices (implants, tools, and anchors, etc.) and related methods useful for anterior or posterior prolapse repair with other treatments for pelvic floor disorders such as urinary incontinence, pelvic floor decent (levator avulsion), and/or sacral fixation. Exemplary levator ani support devices can be introduced through a vaginal incision to tie in with conventional transvaginal mesh repairs and other applications, or can be introduced abdominally (e.g., laparoscopically).

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
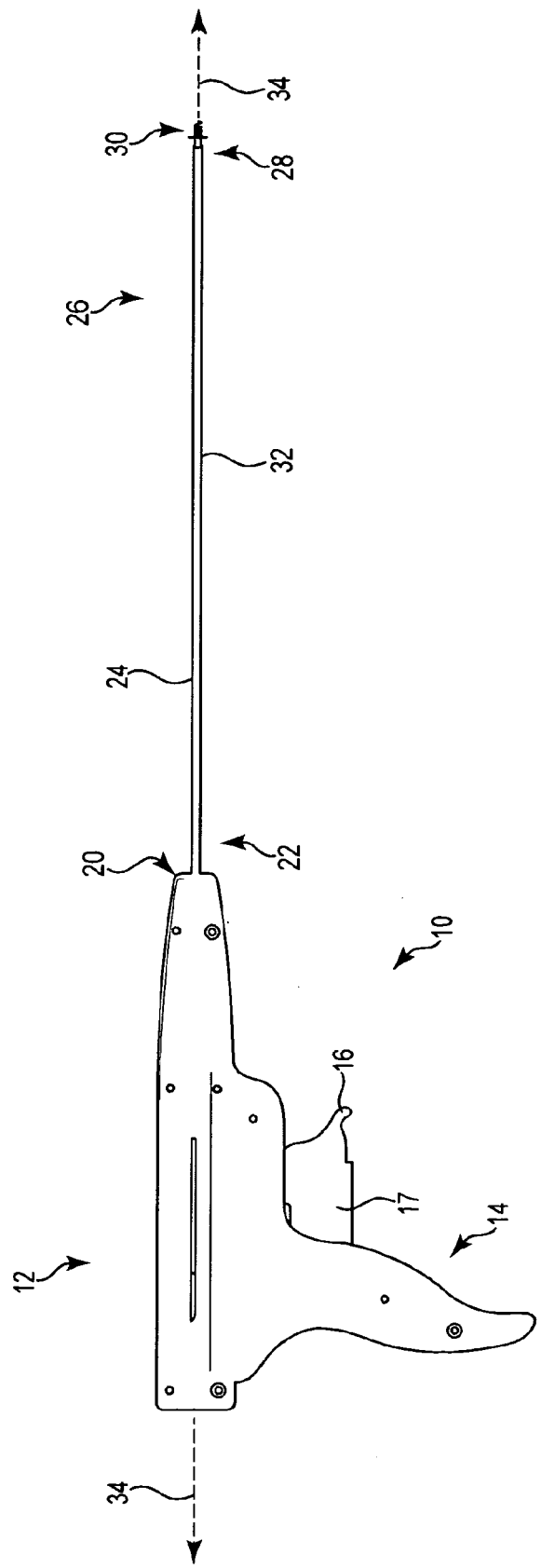
FIG. 1 is a side view of an embodiment of an anchor insertion tool, in accordance with the invention.

The methods and tools as described can be useful in procedures for supporting vaginal tissue, including but not limited to sacral colpopexy procedures (e.g., transvaginal, laparoscopic, and abdominal), along with procedures for treating vaginal vault prolapse caused by rectocele, cystocele, enterocele, and other causes. A sacral colpopexy is a procedure for providing vaginal vault suspension, which can be accomplished with the use of an implant, such as a strip of mesh or other material that attaches to posterior vaginal tissue (e.g., a vaginal cuff) to a region or component of sacral anatomy such as the sacrum (bone itself), a nearby sacrospinous ligament, uterosacral ligament, or anterior longitudinal ligament at the sacral promontory, such as may be accomplished using bone screws or anchors that are implanted into the sacrum. An implant such as a synthetic mesh can be carefully customized or assembled into a special shape by the surgeon. In some sacral colpopexy procedures that also involve a hysterectomy, an implant can alternatively be attached to posterior vaginal tissue that remains after removal of the uterus and cervix, and also to anatomy to support the vaginal tissue at or around the sacrum, such as to uterosacral ligaments or to the sacrum itself (i.e., to a component of the sacral anatomy).

Many of the implants discussed herein include the use of an anchor, as will be described in further detail relative to the present invention. As used herein, the term "anchor" refers non-specifically to any structure that can connect an implant to tissue of a pelvic region. The tissue may be bone or a soft tissue such as a muscle, fascia, ligament, tendon, or the like. Certain methods, implants, and anchors of the present description incorporate a helical anchor such as a screw or coil that can be inserted (e.g., driven) into tissue, preferably soft tissue such as an anterior longitudinal ligament, by rotating about a longitudinal axis upon which the helical anchor advances into the tissue in a longitudinal direction. Other methods may include an anchor in the form of a "self-fixating tip," which can be inserted by pushing the anchor using a straight or curved needle.

An embodiment of the invention is directed generally to surgical instruments, assemblies, and implantable articles for treating pelvic floor disorders such as various forms of prolapse. According to embodiments described herein, a surgical implant can be used to treat a pelvic condition, including the specific examples of surgically placing a surgical implant to treat a pelvic condition such as vaginal vault prolapse. Described herein are various features of surgical implants, surgical tools, surgical systems, surgical kits, and surgical methods useful for installing implants.

One embodiment of an implant that can be used to treat such pelvic disorders is an implant that includes a tissue support portion used to support pelvic tissue such as vaginal tissue, along with one or more extension portions. During use, the tissue support portion can be placed in contact with and attached to tissue to be supported, such as through the use of sutures. An implant of this type can additionally include one or more extension portions attached to the tissue support portion. Optionally a tissue fastener (e.g., a soft tissue anchor or self-fixating tip) can be included at an end of an extension portion, with the tissue fastener and extension portion(s) being designed to attach to tissue in the pelvic region to secure the distal end of the extension portion to the tissue.

The tissue support portion of the above-described implant is designed to support a specific portion of vaginal tissue (anterior, posterior, apical, etc.), depending on the defect that is to be corrected. The tissue support portion can be sized and shaped to contact the desired tissue when installed (e.g., as a "sling" or "hammock"), to contact and support vaginal tissue. A tissue support portion that is located between two or more extension portions may be refereed to as a "central support portion" or a "support portion." The tissue support portion may comprise a number of different materials, such as tissue (e.g., porcine tissue), mesh, or other materials or combinations of materials.

Extension portion(s) of the above-described implant can be elongate pieces of material that extend from the tissue support portion and are useful to pass through or attach to tissue of the pelvic region to thereby provide support for the tissue support portion and the supported tissue. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip or another form of tissue fastener) to thereby provide support for the tissue support portion and the supported tissue. One or more extension portions can extend from a tissue support portion for attachment to tissue in the pelvic region, such as by extending through a tissue path to an internal anchoring point (for attachment by bone anchor, tissue fastener, etc.), or to an external incision.

An extension portion piece can be connected at one end by an anchor (e.g., a self-fixating tip or a helical anchor) to tissue of a pelvic region, such as at a component of sacral anatomy. A second end of the extension portion piece can be connected by way of an adjusting engagement, to the support portion piece. The adjusting engagement may include a frictional engagement element such as a grommet, a one-way or a two-way frictional adjusting element, or the like. The support portion piece, in turn, can contact and support tissue, such as vaginal tissue, in treating vaginal prolapse.

Exemplary implants can be made of materials and may be generally shaped and sized according to previous implants, but modified to include features as described herein, such as a frictional adjusting element, multi-piece construction, a multi-layer tissue support portion, etc. For example an implant can have features as described in the following exemplary documents: U.S. patent application Ser. No. 10/834,943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International Patent Application No PCT/US2006/028828, having an International Filing Date of Jul. 25, 2006; the entireties of each of these disclosures being incorporated herein by reference.

Exemplary implants can be made of materials and exhibit general size and shape features that might be similar to those sold commercially by American Medical Systems, Inc., of Minnetonka, Minn., under the trade names "Apogee", "Perigee", and "Elevate" for use in treating pelvic prolapse (including vaginal vault prolapse, cystocele, enterocele, etc.). In addition, these implants can include portions or sections that are synthetic and/or made of biological material (e.g., porcine, cadaveric, etc.). Extension portions, which may be made of a single piece of material or of multiple pieces of material, may be a synthetic mesh, such as a polypropylene mesh, while the tissue support portion may be synthetic (e.g., a polypropylene mesh) or biologic.

Types of exemplary implants that can be generally useful as discussed herein can include those previously and currently used in treating pelvic conditions, including those implants referred to as "slings," "strips," "mesh strips," "hammocks," among other terms for pelvic implants. Particular examples of implants for treating vaginal prolapse can include a central support portion and from two to four to six extension portions, and may take the form of an integral piece of mesh or multiple pieces of mesh attached in a modular fashion. See, e.g., Assignee's copending U.S. patent application Ser. Nos. 11/398,369; 10/834,943; 11/243,802; 10/840,646; PCT/2006/028828; among others.

Another embodiment of an implant that can be used to treat certain pelvic disorders in accordance with the invention is an implant that includes a preassembled implantable article, which can reduce challenges faced by a surgeon by eliminating the need to create a customized implantable article for surgical procedures. One particular embodiment is an implant that is preassembled into a Y-shape that includes a base portion and a head portion, wherein the head portion comprises first and second tissue engagement portions, each of which extends from the base portion. The first and second tissue engagement portions can be secured to the base portion using a wide variety of configurations and materials, such as using a configuration that distributes forces that would otherwise tend to separate one or both of the tissue engagement portions from the base portion. Such a configuration may include the use of biocompatible materials such as tissue adhesives, tissue sealants, biocompatible bonding agents (e.g. silicone), and biocompatible adhesives. Alternatively, RF or ultrasonic welding or heat sealing may be used alone or in conjunction with other techniques to create a separation force distribution means.

In an embodiment of a preassembled implant, the implant can include a plurality of pores that afford tissue ingrowth and resist infection, and can include a backing that is coated. The backing material may include one or more woven, knitted or inter-linked filaments or fibers that form multiple fiber junctions, and/or may include monofilament and multifilament embodiments. The fiber junctions may be formed via weaving, bonding, ultrasonic welding, knitting or other junction forming techniques, including combinations thereof. In addition, the size of the resultant openings or pores of the implantable article should be sufficient to allow tissue in-growth and fixation within surrounding tissue.

The preassembled implant may be made of a variety of materials including, but not limited to, Prolene™, nylon, polypropylene, Deklene™, poly-L-lactide (PLLA), polyethylene glycol (PGA), polyester and any combination of materials. Depending on the desired treatment, the implant or portions thereof, may be absorbable, non-absorbable and/or resorbable. Non-synthetic structures are also included within the scope of the invention. Other synthetic and non-synthetic materials suitable for use for the implants include, but are not limited to, synthetic biomaterials, allografts, homografts, heterografts, autologous tissues, materials disclosed in U.S. Provisional Application Ser. Nos. 60/263,472, Ser. No. 60/281,350 and Ser. No. 60/295,068 (the contents of which are incorporated herein by reference), synthetic materials (such as metallics, polymerics, and plastics) and any combination of such materials. Specific examples of suitable synthetic materials that can be used include, but are not limited to, polypropylene, polyester, polyethylene, nylon, PLLA and PGA. The material can generally be selected from materials that cause minimal to no reaction with body tissues and fluids and that will retain its particular material characteristics/properties indefinitely or for a predetermined length of time. Portions or all of the material may be resorbable if consistent with the desired surgical procedure.

Dimensions of any of the implants of the invention can be as are determined to be useful for any particular installation procedure, treatment, patient anatomy, and to support a specific tissue or type of tissue. Exemplary dimensions can be sufficient to allow the tissue support portion to contact tissue to be supported, and to allow extension portions to extend from the tissue support portion to a desired anatomical location to allow the extension portion to be secured to or pass through tissue of the pelvic region and support the tissue support portion.

A distal end of an extension portion, according to embodiments of the invention, can include a tissue fastener that attaches to tissue of the pelvic region. The tissue fastener can be, e.g., a soft tissue anchor, a self-fixating tip, a biologic adhesive, a tissue clamp, opposing male and female connector elements that securely engage when pushed together, or any other device to secure a distal end of an extension portion to tissue of the pelvic region. The implant may also have extension portions that do not include a tissue fastener at a distal end of an extension portion, for example if the distal end is designed to be secured to tissue by other methods (e.g., suturing), or is intended to pass through an external incision. During installation of the implant, the tissue fastener can be secured to any desired tissue, for example fibrous tissue such as a muscle, a ligament and/or its surrounding tissue, or a tendon and/or its surrounding tissue; or tissue at or near the ischial spine.

In an exemplary implantation procedure for an implant that includes a tissue portion and one or more extension members, a portion of the implant, such as an extension portion, can be placed at and passed through soft support tissue of the pelvic region, to lead and pass the extension portion through the soft support tissue. The soft support tissue can be any tissue desired or useful to which to attach an extension portion, for example any of the following: muscle tissue of an obturator foramen (e.g., obturator internus muscle), tissue of an arcus tendineus or surrounding an arcus tendineus, tissue of a sacrospinous ligament, tissue in a region of a sacrospinous ligament, tissue of a coccyx region, tissue of a region of an ischial spine, tissue of coccygeous muscle, tissue of iliococcygeous muscle, tissue of a uterosacral ligament, tissue of levator muscle, or combinations of these. Tissue in a "region" of an ischial spine can be tissue that is within one centimeter of an ischial spine, including tissue of the levator ani muscle (e.g., iliococcygeous muscle) and arcus tendineus.

When placing an extension portion through soft support tissue, embodiments of the invention can lead the extension portion into the a surface of soft support tissue at an insertion location, pass the extension portion through a mass of one or more types of soft support tissue, then exit the soft support tissue at an exit location on the surface of soft support tissue. The insertion location and the exit location can both be located at surfaces of a single side of tissue, generally at surfaces on the side of the tissue that can be accessed within the pelvic region, e.g., from a perineal incision, a vaginal incision, or an abdominal incision. In other words, the extension portion enters on one side of tissue (generally on the side within the pelvic region), passes laterally or "tunnels" through a length of soft support tissue, then exits in the direction substantially opposite of the direction of insertion, returning into the pelvic region. The extension portion does not traverse soft support tissue by entering into one side of tissue, traversing the thickness of the tissue, and exiting the other side.

According to certain embodiments, the insertion and exit locations, at tissue surfaces on the same side of tissue, can be at surfaces of the same tissue, e.g., if both of the insertion and exit locations are located at surfaces of the same muscle, ligament, or tendon. For example, the extension portion enters soft support tissue at a surface on one side of coccygeus muscle; the extension portion passes laterally through a length of coccygeus muscle, e.g., tunneling sideways or laterally through the muscle; and the extension portion then exits the coccygeus muscle through an exit location at a surface on the same side of the muscle as the insertion location. Alternately, the extension portion can enter soft support tissue at a surface on one side an obturator internus muscle; the extension portion can pass laterally through obturator internus muscle, e.g., tunneling sideways or laterally through the muscle; and the extension portion can then exit the obturator internus muscle through an exit location at a surface on the same side of the obturator internus muscle as the insertion location.

According to other embodiments of the invention, the exit location and the insertion location can be located on nearby, adjacent, or proximate locations of nearby or neighboring tissues, e.g., adjacent surface of different muscle, ligament, tendon, or combinations of these. For example, the extension portion can enter soft support tissue at a surface on one side of coccygeus muscle; the extension portion can pass through the coccygeus muscle, e.g., tunneling sideways or laterally through the muscle and to a location behind a sacrospinous ligament; the extension portion can then exit the at a surface of the sacrospinous ligament through an exit location on the side of the ligament that is adjacent to the insertion location on the coccygeus muscle.

Another example of a location for attaching an end of an extension portion is at a tissue path that passes through, or terminates at, a coccyx region as described in Applicant's copending U.S. patent application Ser. No. 11/398,368, filed Apr. 5, 2006, the entirety of which is incorporated herein by reference. That application describes the use of an implant to treat vaginal prolapse (e.g., vault prolapse, enterocele, cystocele, rectocele) using an implant that includes a tissue support portion and extension portions, wherein extension portions are passed through a tissue path that includes a region of the coccyx bone (i.e., a "coccyx region" or a "transcoccyx" tissue path).

Exemplary methods involve placement of a support member to support prolapsed tissue, including placement of an extension portion of the support member at coccyx region, proximal to the coccyx bone, e.g., attached to or extending through muscle (e.g., ischiococcygeous muscle, iliococcygeous muscle), or ligament (sacrospinous ligament) lateral to the coccyx bone. Exemplary tissue paths can initiate from a region surrounding vaginal vault tissue and can extend past the rectum to a location proximal to the coccyx bone. An extension portion of the support member can generally be guided through such a passage prepared in muscle or other tissue, past the rectum, proximal to the coccyx bone, and attached to tissue internally in this region. A distal end of an extension portion can attach to any tissue of the coccyx region, such as with a tissue fastener securing a distal end of extension portion to muscle or ligament (e.g., sacrospinous ligament) in the coccyx region. Alternately, the distal end of extension portion can extend through tissue of the coccyx region and to an external incision of the epidermis.

As used herein, the term "anchor" refers non-specifically to any structure that can connect an implant to tissue of a pelvic region. The tissue may be bone, or a soft tissue such as a muscle, fascia, ligament, tendon, or the like. Preferred methods, implants, and anchors of the present description incorporate a helical anchor such as a screw or coil that can be inserted (e.g., driven) into tissue, preferably soft tissue such as an anterior longitudinal ligament, by rotating about a longitudinal axis upon which the helical anchor advances into the tissue in a longitudinal direction.

Referring generally to the figures, various embodiments and views of tools (e.g., "drivers," or "insertion tools") are shown for use in methods for treating pelvic conditions. Various portions of a tool can be constructed of polymer materials, metal, or other biocompatible or acceptable surgical apparatus materials.

Embodiments of insertion tools (or "drivers") can include a proximal end having a handle and an actuator, trigger, or both. The proximal end of the tool, e.g., the handle, is attached to a proximal end of a shaft, which includes an outer shaft (e.g., a hollow tube or sheath), and an inner rotating shaft. The outer shaft extends to a distal shaft end, and the inner rotating shaft extends to the distal shaft end. The length of the shaft (including the outer shaft and the inner rotating shaft) is sufficient to allow a user to grasp and manipulate the proximal end (e.g., at the handle and actuator), as the shaft is placed at a location of a posterior pelvic region, e.g., to place the distal shaft end at a location for placing an anchor at a component of sacral anatomy, such as an anterior longitudinal ligament at a sacral promontory. Exemplary lengths between a proximal and a distal end of a shaft may be in the range from 10 to 30 centimeters (e.g., from 13 to 18 centimeters), especially for use in a female patient to access a posterior location of a pelvic region such as a region of sacral anatomy.

The shaft includes a longitudinal axis, and a distal end or "tip." The tip is capable of engaging and holding (for manipulation) a helical anchor for insertion (e.g., through a vaginal incision) to a location of a posterior pelvic region where the helical anchor can be fastened to tissue. The helical anchor includes a proximal end and a distal end, the proximal end being capable of engaging with the shaft, and the distal end being capable of being placed in contact with tissue. With the proximal end of the anchor engaged at the tip, and the distal end of the anchor in contact with tissue, the inner rotating shaft can be rotated along its longitudinal axis, causing the helical anchor to rotate around a co-linear longitudinal axis of the helical anchor. The distal end of the helical anchor advances into the tissue upon such rotation.

The proximal end of the tool includes an engagement between the actuator and the proximal end of the inner rotating shaft, the engagement being capable of causing the inner rotating shaft to rotate upon movement of the actuator. In certain specific embodiments the engagement is capable of translating linear or curved-linear motion of the actuator into rotational movement of the inner rotating shaft. As the actuator is moved to cause rotational movement of the inner rotating shaft, a helical anchor engaged with the inner rotating shaft at the distal end of the inner rotating shaft rotates along a longitudinal axis in a manner that allows the anchor to be rotationally advanced (e.g., driven) into tissue.

Referring more specifically to the Figures, FIG. 1 is a side view of a exemplary embodiment of an insertion tool or "driver." Driver 10 includes proximal portion 12, which includes a handle 14, an actuator 17, and a trigger 16. A shaft 24 extends from an end 20 of proximal portion 12, wherein the shaft 24 comprises a proximal shaft end 22, a distal end 26, and tip 28. An exemplary helical anchor 30 is shown as being positioned for engagement with tip 28. The length of shaft 24 is sufficient to allow a user to grasp and manipulate handle 14 with shaft 24 and to thereby place distal shaft end 26, tip 28, and helical anchor 30 at a desired location, such as at a location of a posterior pelvic region (e.g., to place the distal shaft end at a location for placing helical anchor 30 at a component of sacral anatomy). Shaft 24 includes an outer shaft 32 and an inner rotating shaft (not visible in this Figure). When actuator 17 is moved in a proximal direction relative to handle 14, such as by squeezing the components together, the inner rotating shaft rotates about a rotational (longitudinal) axis 34, causing helical anchor 30, which is engaged with the inner rotating shaft at tip 28, to rotate about the same axis 34 (which can also coincide with a longitudinal axis of the helical anchor 30). Tool 10 of FIG. 1 can be designed as a "two-pull" driver, such that the actuator 17 can be actuated or pulled proximally two (or optionally more than two) times to produce a certain amount of rotational movement of helical anchor 30 to drive it into tissue.

Figure 2:
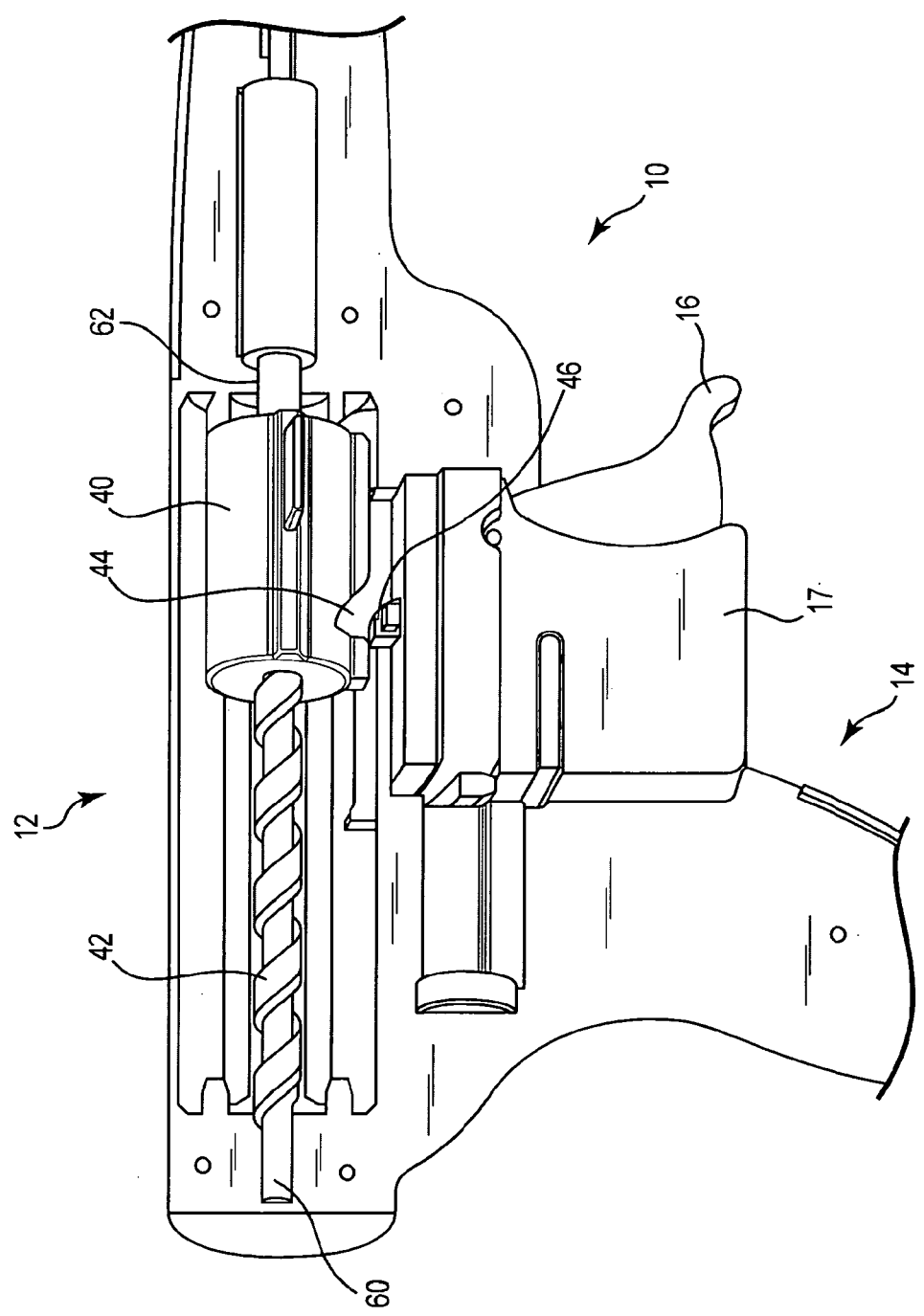
FIG. 2 is perspective view of the anchor insertion tool of FIG. 1 with a side cover removed.

FIG. 2 illustrates a cut-away view of tool 10 to better show an exemplary configuration of its components. As shown, the tool 10 further includes a cylindrical rider or barrel 40 having a notch 44 extending from its outer surface toward its longitudinal axis. Notch 44 is engageable with an extendible (and retractable) latch 46 of actuator 17. Tool 10 further includes a proximal threaded portion 42 of the inner rotating shaft, which is held proximally and distally at bearings 60 and 62, and which extends through the barrel 40. Extendible latch 46 is extendible and retractable by movement of trigger 16 (e.g., proximally and distally, respectively) relative to the body of actuator 17. Barrel 40 includes internal threads or another type of engagement structure to facilitate engagement with external threads of threaded portion 42 to thereby allow for linear movement of rider 40 along threaded portion 42 and cause rotation of the inner rotating shaft. It is noted that the rotation can be clockwise or counter-clockwise, depending on the design of the helical anchor.

Figure 3:
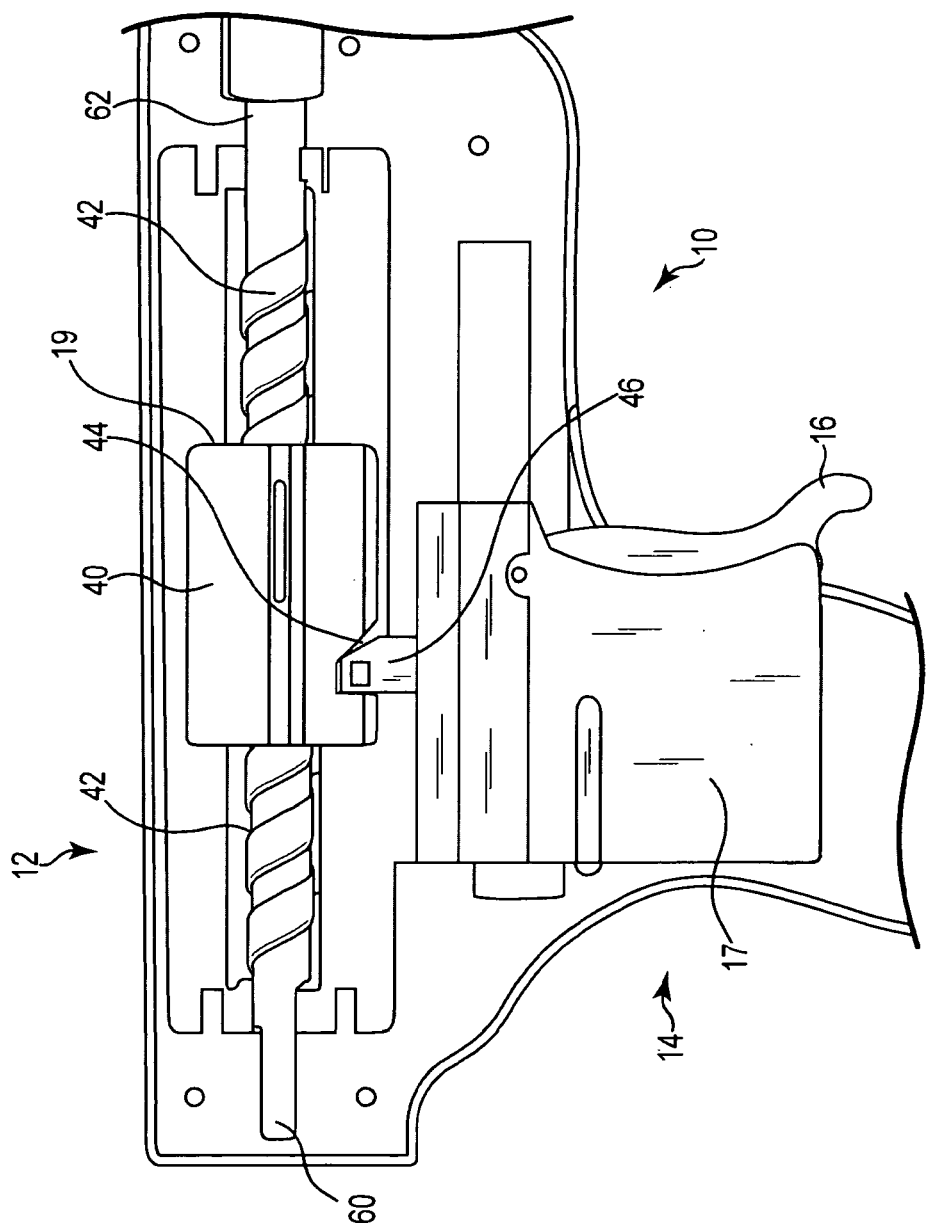
FIG. 3 is a side view of the anchor insertion tool of FIG. 1 with a side cover removed.

FIG. 2 shows barrel 40 in one of its activation configurations, wherein the barrel 40 is generally positioned at a distal location of threaded portion 42, actuator 17 is positioned at a forward location, and latch 46 is in a retracted position. Latch 46 can optionally be spring-biased. Latch 46 is extendible into notch 44 by movement of trigger 16 in a proximal direction. When trigger 16 is moved in this manner, handle 14 will extend latch 46 to engage with notch 44. Subsequent movement of actuator 17 in a proximal direction, as is shown in FIG. 3, causes barrel 40 to move proximally along threaded portion 42, thereby causing rotation of the proximal threaded portion 42 and the inner rotating shaft.

Figure 4:
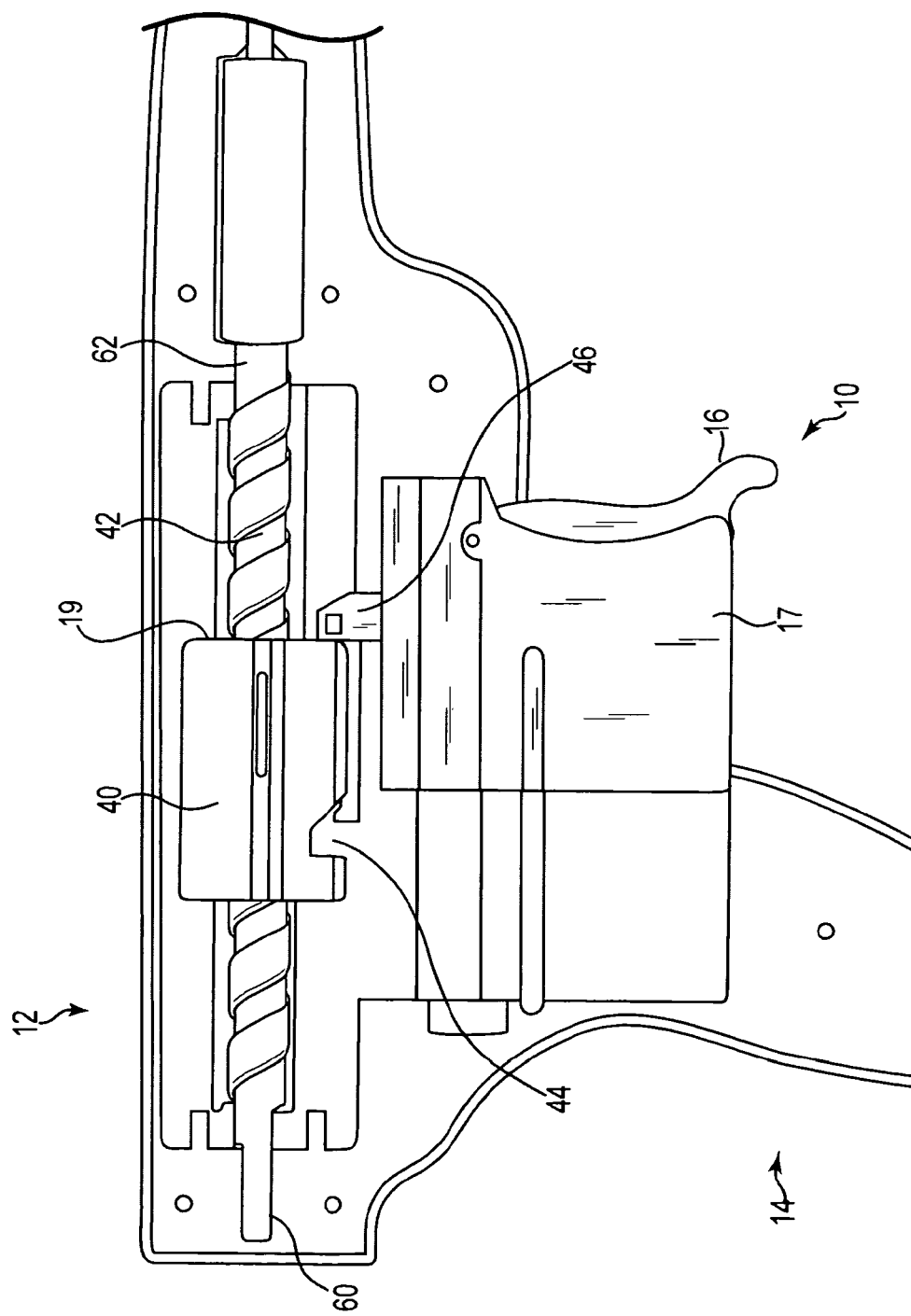
FIG. 4 is another side view of the anchor insertion tool of FIG. 1 with a side cover removed.

Actuator 17 can be biased to then move distally by releasing pressure on it, such as can be caused by a spring or other component that will move the actuator in a distal direction. Latch 46 is then retracted and moves distally, until it is adjacent to a distal face 19 of barrel 40. Latch 46 can then be extended by proximal movement of trigger 16 so that it comes into contact with the distal face 19 of barrel 40, as is illustrated in FIG. 4. Further movement of actuator 17 in a proximal direction will cause barrel 40 to move further proximally along threaded portion 42, thereby causing additional rotation of the inner rotating shaft and associated anchor 30. Actuator 17 will then move further to a proximal location, such as can be caused by a spring or other component, for example. At this point, the trigger 16, which may be spring-loaded, will be in the forward position and the anchor will be driven into the target tissue. In order to reset the mechanism, such as to deliver an additional anchor, one or more tabs that extend from the outer surface of the barrel 40 can be pushed in a distal direction, for example.

Figure 5:
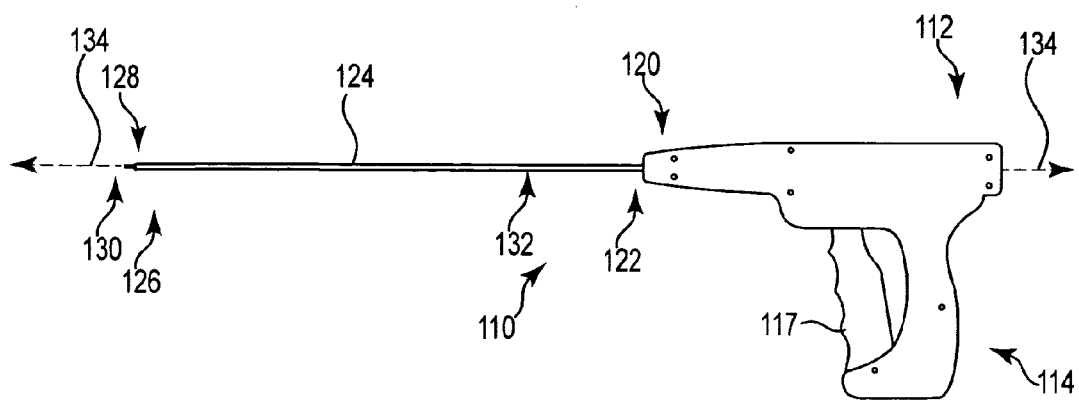
FIG. 5 is a side view of an embodiment of an anchor insertion tool, in accordance with the invention.
Figure 6:
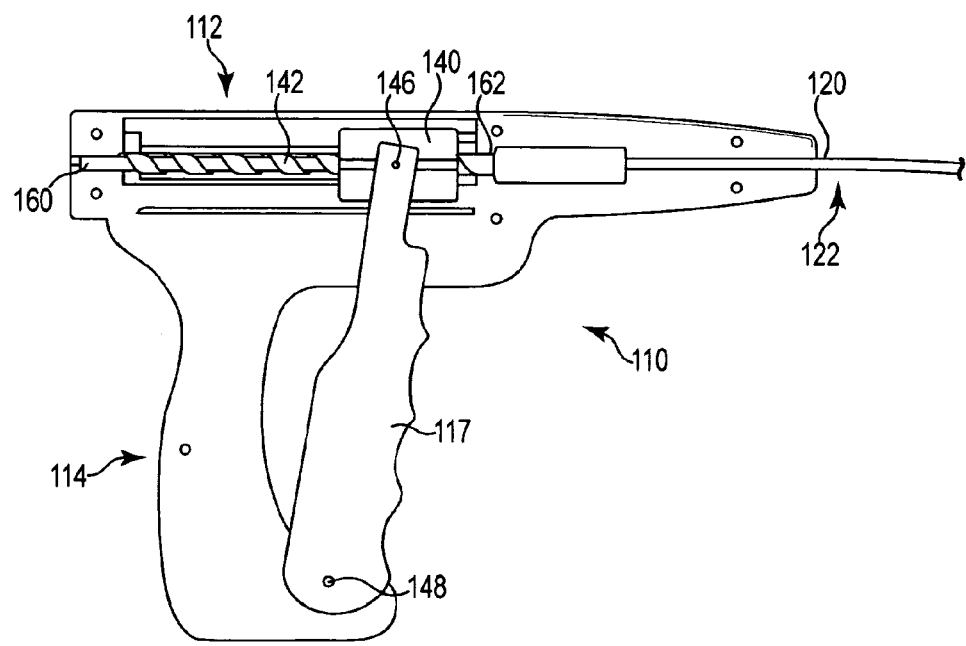
FIG. 6 is a side view of the anchor insertion tool of FIG. 5 with a side cover removed.
Figure 7:
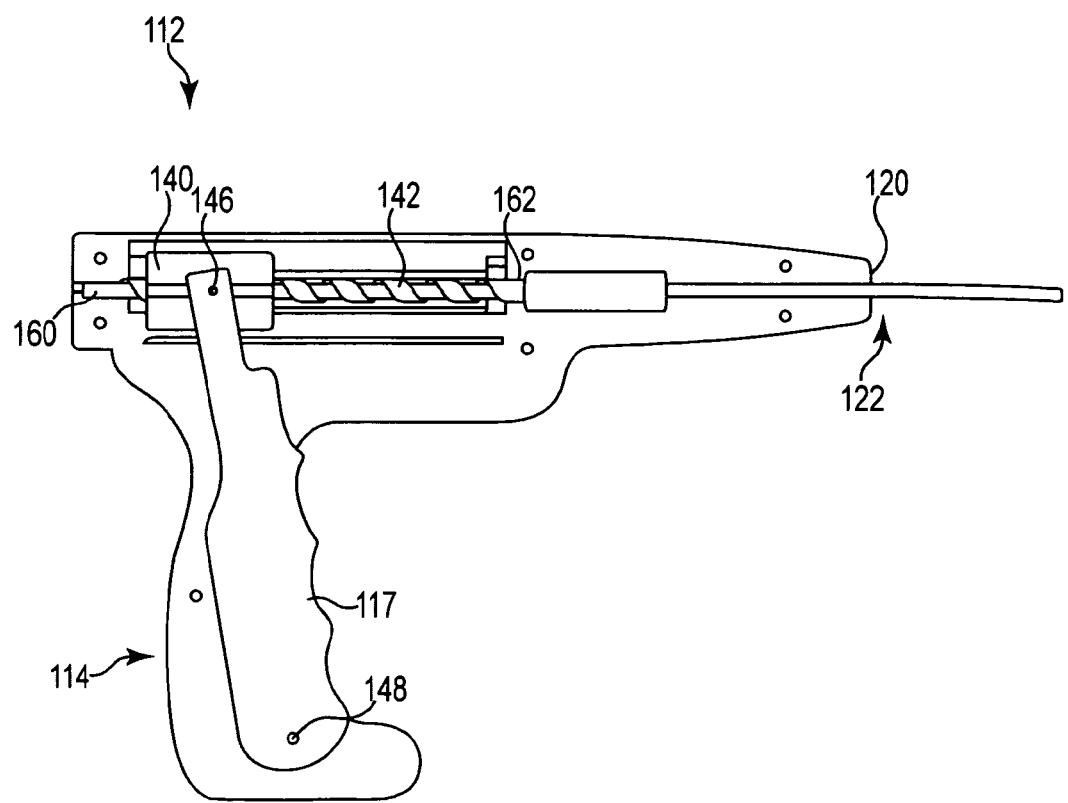
FIG. 7 is another side view of the anchor insertion tool of FIG. 5 with a side cover removed.

Another exemplary embodiment of an anchor insertion tool or driver 110 is illustrated in FIGS. 5-7. Driver 110 generally includes a proximal portion 112, which includes a handle 114 and an actuator 117. A shaft 124 extends from an end 120 of proximal portion 112, wherein the shaft 124 comprises a proximal shaft end 122, a distal end 126, and tip 128. An exemplary helical anchor 130 is shown as being positioned for engagement with tip 128. The length of shaft 124 is sufficient to allow a user to grasp and manipulate handle 114 with shaft 124 to thereby place distal shaft end 126, tip 128, and helical anchor 130 at a desired location, such as at a location of a posterior pelvic region (e.g., to place the distal shaft end at a location for placing helical anchor 130 at a component of sacral anatomy). Shaft 124 includes an outer shaft 132 and an inner rotating shaft (not visible in this figure). When actuator 117 is moved in a proximal direction relative to handle 114, the inner rotating shaft rotates about a rotational (longitudinal) axis 134, thereby causing helical anchor 130, which is engaged with the inner rotating shaft at tip 128, to rotate about the same axis 134 (which can also coincide with a longitudinal axis of the helical anchor 130). Tool 110 of FIGS. 5-7 can be designed as a "one-pull" driver, meaning that actuator 117 can be actuated or pulled proximally relative to handle 114 a single time, (e.g., one stroke produces a desired amount of rotational movement of helical anchor 130 to drive it into tissue).

FIG. 6 illustrates a cut-away view of tool 110 to better show an exemplary configuration of its components, including proximal end 112, handle 114, and actuator 117. FIG. 6 additionally shows a cylindrical rider or barrel 140 attached to an upper end of actuator 117 at an upper attachment area 146, which may be a slide or a pivot, for example. A lower end of actuator 117 is attached to a lower end of handle 114 at a lower attachment area 148, which also may be a slide or a pivot. A proximal threaded portion 142 of the inner rotating shaft is held proximally and distally at bearings 160 and 162, respectively. FIG. 6 illustrates barrel 140 at its "start" position, where it is located at a generally distal end of threaded portion 142. Barrel 140 includes internal threads (or other structure, not shown) for engagement with external threads of threaded portion 142 that allow linear movement of barrel 140 along threaded portion 142 (e.g., in a proximal direction), to cause rotation of the inner rotating shaft.

To activate the tool 110, actuator 117 can be moved proximally relative to handle 114 by squeezing it toward the handle 114. This movement may involve pivoting movement, sliding movement, or both pivoting and sliding movement at upper attachment 146 (between the upper end of actuator 117 and rider 140), and also at lower attachment 148 (between the lower end of actuator 117 and handle 114). Advantageously, a single movement or "stroke" of the upper end of actuator 117 between the "start" position and a "final" position (as shown in FIG. 7) can cause barrel 140 to traverse the full length of threaded portion 142, causing an amount of rotational movement of inner shaft 133 that is sufficient to rotate a helical anchor (such as helical anchor 130, which is engaged with tip 128) a sufficient number of rotations (e.g., from 1 to 10 rotations, such as from 2 to 5 rotations) to cause the helical anchor to be fully driven into tissue. Thus, FIG. 7 can be considered to show the "final" position of actuator 117 and barrel 140 at a proximal location of proximal end 112, which is how the tool 110 will be configured after barrel 140 has been moved proximally along the length of threaded portion 142 by a single stroke of actuator 117 in a proximal direction.

Figure 8:
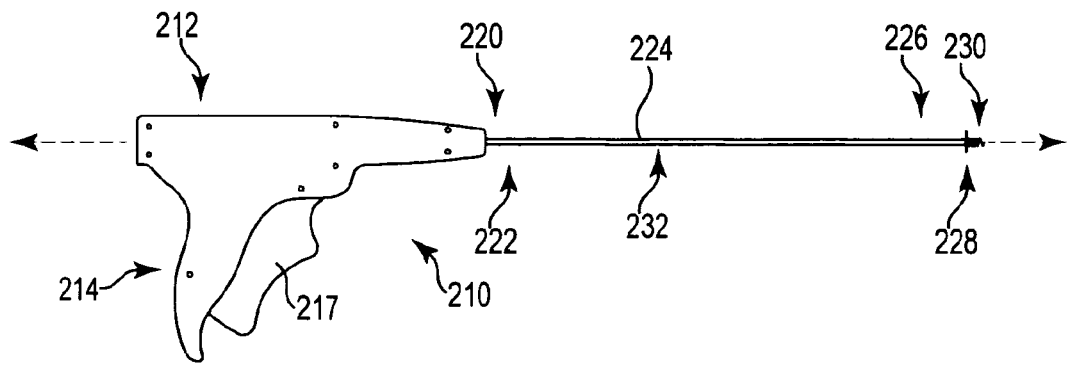
FIG. 8 is a side view of an embodiment of an anchor insertion tool, in accordance with the invention.
Figure 9:
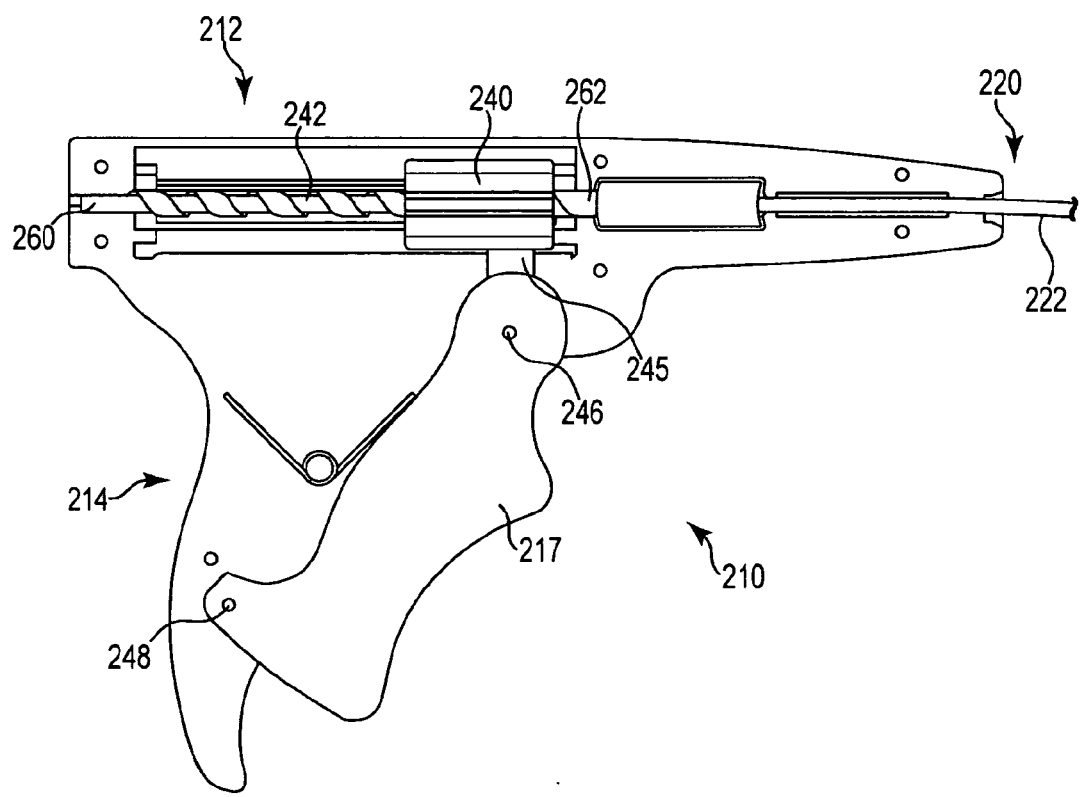
FIG. 9 is a is a side view of the anchor insertion tool of FIG. 8 with a side cover removed.
Figure 10:
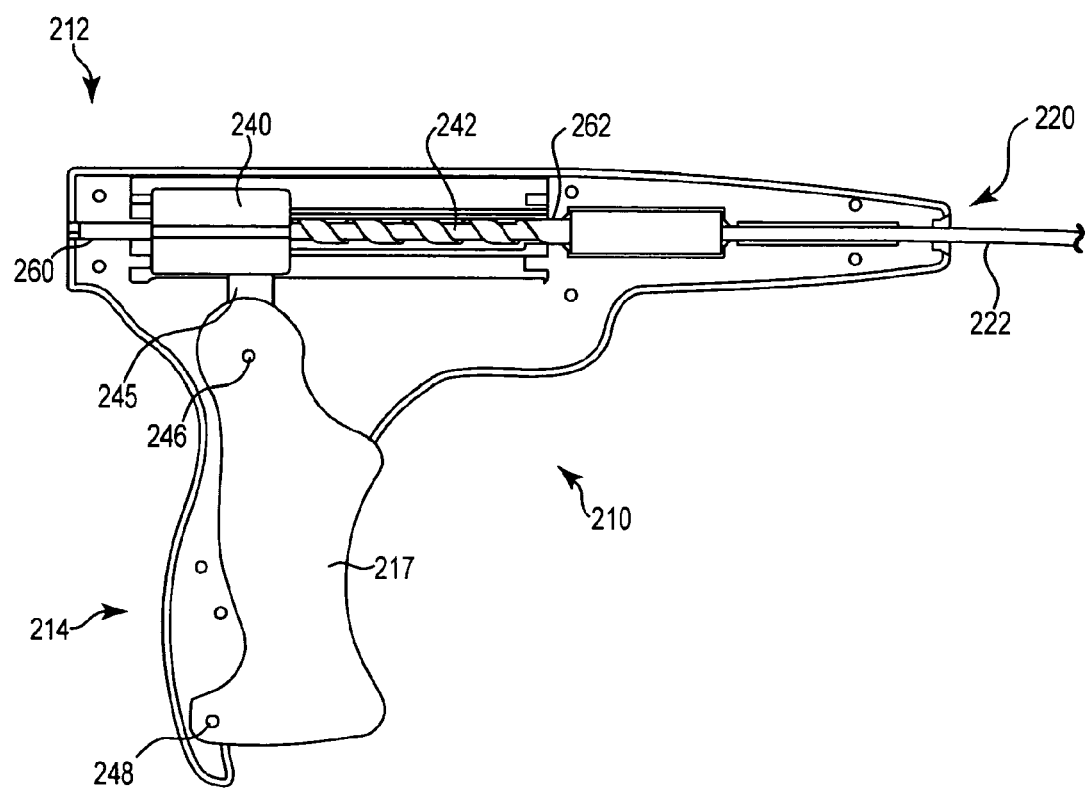
FIG. 10 is another side view of the anchor insertion tool of FIG. 8 with a side cover removed.

Another exemplary embodiment of an anchor insertion tool or driver 210 is illustrated in FIGS. 8-10. Driver 210 generally includes a proximal portion 212, which includes a handle 214 and an actuator 217. A shaft 224 extends from an end 220 of proximal portion 212, wherein the shaft 224 comprises a proximal shaft end 222, a distal end 226, and tip 228. An exemplary helical anchor 230 is shown as being positioned for engagement with tip 228. The length of shaft 224 is sufficient to allow a user to grasp and manipulate handle 214 with shaft 224 to thereby place distal shaft end 226, tip 228, and helical anchor 230 at a desired location, such as at a location of a posterior pelvic region (e.g., to place the distal shaft end at a location for placing helical anchor 230 at a component of sacral anatomy). Shaft 224 includes an outer shaft 232 and an inner rotating shaft (not visible in this figure). When actuator 217 is moved in a proximal direction relative to handle 214, inner rotating shaft 233 rotates about its rotational (longitudinal) axis 234, thereby causing helical anchor 230, which is engaged with the inner rotating shaft at tip 228, to rotate about the same axis 234 (which can also coincide with the longitudinal axis 234 of helical anchor 230). Tool 210 of FIGS. 8-10 can be designed to be a "one-pull" driver, such that actuator 217 can be actuated or pulled proximally relative to handle 214 a single time to produce a desired amount of rotational movement of helical anchor 230 to drive it into tissue.

FIG. 9 illustrates a cut-away view of tool 210 to better show an exemplary configuration of its components, including proximal end 212, handle 214, and actuator 217. FIG. 9 additionally shows a cylindrical rider or barrel 240 attached through barrel extension 245 to an upper end of actuator 217 at an upper attachment area 246, which may be a slide or a pivot, for example. A lower end of actuator 217 is attached to a lower end of handle 214 at a lower attachment area 248, which also may be a slide or a pivot. A proximal threaded portion 242 of the inner rotating shaft is held proximally and distally at bearings 260 and 262, respectively. FIG. 9 illustrates barrel 240 at its "start" position, where it is located at a generally distal end of threaded portion 242. Barrel 240 includes internal threads (or other structure, not shown) for engagement with external threads of threaded portion 242 that allow linear movement of barrel 240 along threaded portion 242 (e.g., in a proximal direction), to cause rotation of the inner rotating shaft.

To activate the tool 210, actuator 217 can be moved proximally relative to handle 214, such as can be accomplished by squeezing these components together. This movement may involve pivoting movement, sliding movement, or both pivoting and sliding movement at upper attachment 246 (between the upper end of actuator 217 and barrel extension 245 of rider 240), and also at lower attachment 248 (between the lower end of actuator 217 and handle 214). Advantageously, a single movement or "stroke" of the upper end of actuator 217 between the "start" position and a "final" position (as shown in FIG. 10) can cause rider 240 to traverse the full length of threaded portion 242, causing an amount of rotational movement of inner shaft 233 that is sufficient to rotate a helical anchor (e.g., anchor 230, which is engaged with tip 228) a sufficient number of rotations (e.g., from 1 to 10 rotations, or from 2 to 5 rotations) to cause the helical anchor to be fully driven into tissue. Thus, FIG. 10 can be considered to show the "final" position of actuator 217 and barrel 240, at a proximal location of proximal end 212, such as it can be positioned after barrel 240 has been moved proximally along the length of threaded portion 242 by a single stroke of actuator 217 in a proximal direction.

The tool 210 can further include a slot that is part of the engagement between the lower end of actuator 217 and a location at a lower position of the handle 214. The slot can be curved, and relatively vertical, having a shape that allows linear movement of the upper end of actuator 217 in a proximal direction, while engaging extension 245, which will result in linear, proximal movement of rider 240.

Figure 11:
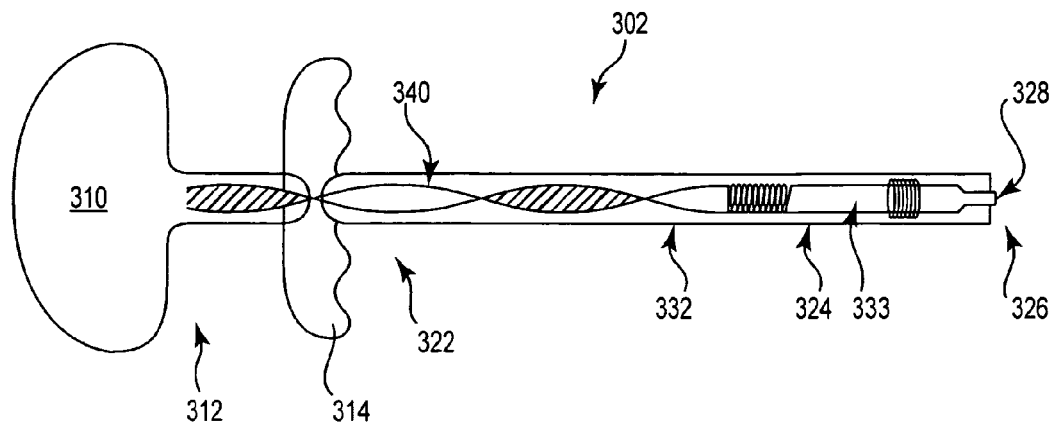
FIG. 11 is a side view of an embodiment of an anchor insertion tool, in accordance with the invention.

Another embodiment of a driver is shown at FIG. 11, which is a side view of an exemplary insertion tool or driver 302. Driver 302 includes a proximal end 312, which includes a palm grip 310 and handle or actuator 314. Proximal end 312 engages a proximal end 322 of a shaft 324, which extends to a distal end 326 and a tip 328. A helical anchor (not shown) can engage with the tip 328. The length of shaft 324 is sufficient to allow a user to grasp and manipulate proximal end 312 so that the distal shaft end 326, tip 328, and a helical anchor will be positioned at a location of a posterior pelvic region (e.g., to place the distal shaft end at a location for placing an anchor at a component of sacral anatomy). Shaft 324 includes an outer shaft 332 and an inner rotating shaft 333. When actuator 314 is moved in a proximal direction relative to palm grip 310, inner rotating shaft 333 rotates about its rotational (longitudinal) axis, thereby causing a helical anchor engaged with inner rotating shaft 333 at tip 328 to rotate about the same axis (which can also coincide with the longitudinal axis of the helical anchor).

Exemplary features of tool 302 include a shaft having a twisted ribbon-like extension 340, along which actuator 314 can be moved linearly to produce rotational movement of shaft 333. Advantageously, the palm grip 310 and overall arrangement of components at proximal end 312 can allow for a user to exert constant pressure on a fixation site during use. Tool 302 can optionally include an anti-reverse rotation mechanism such as a ratcheting feature to prevent the helical anchor from being backed out of a desired position. Tool 302 can further include two clutches or coils, one of which is located between the shaft and the twist ribbon, and the other of which is located between the shaft and tube.

In operation, two clutches of the tool 302 can be useful to drive an anchor into a desired location while keeping the tip 328 steady and allowing rotation in one direction. In one exemplary method of using a tool of the invention, such as driving tool 302, a user (e.g., a physician) can hold the tool 302 with the palm grip 310 resting in the palm of a hand, and then pull back on the handle 314 using his/her fingers. The handle will then slide down the twist ribbon 340, which will rotate. One clutch will then engage and drive the shaft to tighten the screw. The clutch between the shaft and the tube will then engage and allow rotation. When the handle reaches the end of its travel, the handle will move to its original position. The clutch between the shaft and tube then engages to prevent reverse rotation, and then the clutch between the twist ribbon and shaft will disengage to allow rotation. When the handle reaches the end of its travel, the process can be repeated, if desired.

Figure 12:
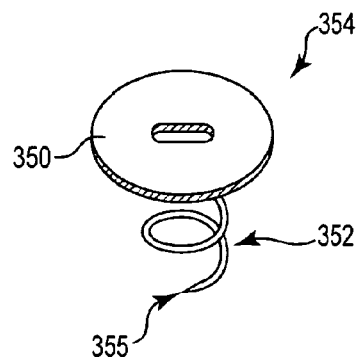
FIG. 12 is a perspective top view of an anchor member that can be used with anchor insertion tools of the invention.

FIG. 12 illustrates an example of a helical anchor 354 that can be used with driver 302 or other tools shown or described herein (e.g., tools designated by reference numbers 10, 110, 210, 302, 402, 502, and 600). Helical anchor 354 includes head 350, which can engage a tip and rotating shaft of a tool. A helical portion 352 extends from a surface of the head 350 and is in the form of a screw, corkscrew, helical coil, open spiral, or the like, having a tip that can enter tissue when helical anchor 354 is rotated about a longitudinal axis 356 by a rotating shaft of a driver. Tip 355 can be pointed or sharpened to function as a leading edge upon entry into and passage through tissue.

Figure 13:
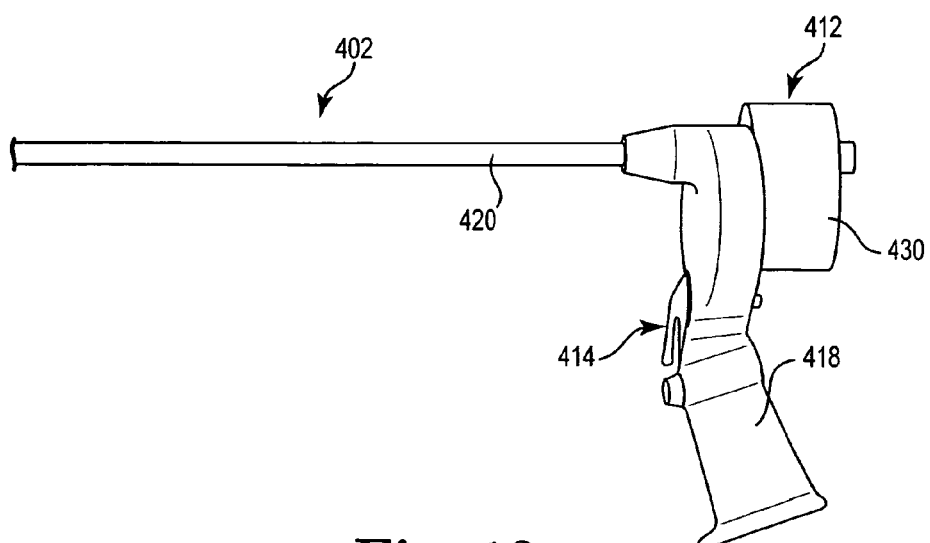
FIG. 13 is a side view of an embodiment of an anchor insertion tool, in accordance with the invention.

FIG. 13 illustrates an exemplary embodiment of a tool 402 that can be used for implanting a bone screw or anchor, which includes at least certain general features as described elsewhere herein, and additionally including a spring coil motor 430 that can cause rotation of an inner rotating shaft. In particular, tool 402 includes a proximal end 412 having a handle 418, an actuator 414, and a shaft 420 that includes a rotating shaft that can be rotated by powered motor 430 located at a proximal end of the device. Optionally, motor 430 can be engaged with the rotating shaft to cause desired torque to drive a helical anchor and to control a number of revolutions of the rotating shaft to an amount that drives the helical anchor a desired depth, e.g., from 2 to 10 rotations, such as from 3 to 4 rotations, optionally 3.5 rotations. The motor may further comprise a friction damper to control the speed of rotation, and may optionally have a pulley ratio that functions in the generally range of 3.5:1, although the ratio can be higher or lower than this ratio. In addition, the proximal end 412 of the tool 402 may include two holes in its outer casing, where one of these holes prevents over rotation if the actuator 414 is held down (i.e., activated), and the second hole allows an operator to initiate the fixation process.

Figure 14:
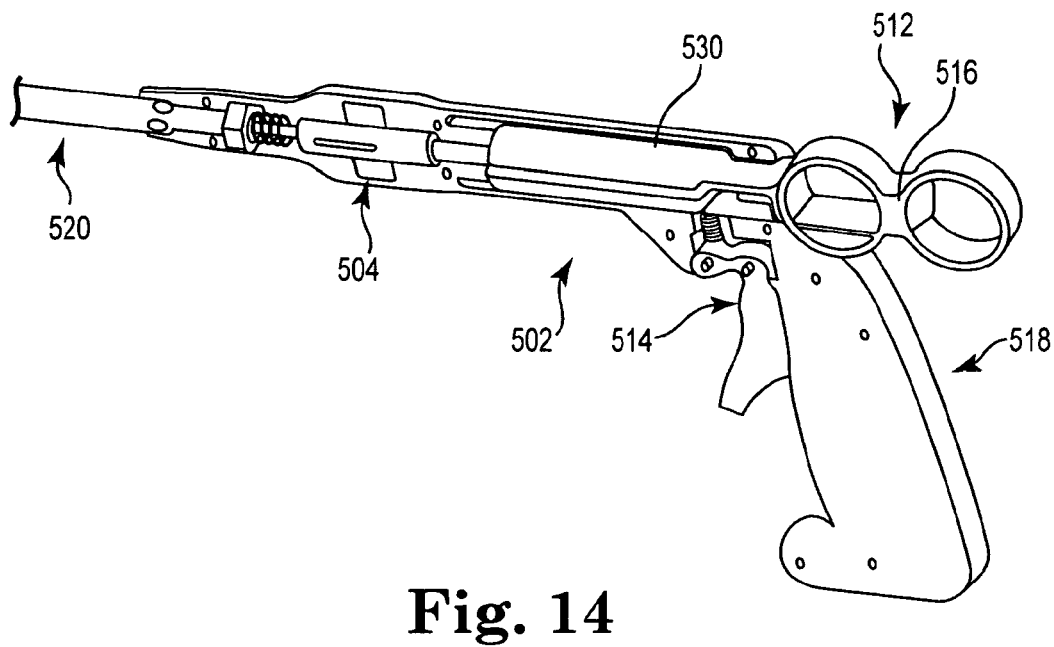
FIG. 14 is a perspective view of an embodiment of an anchor insertion tool, in accordance with the invention.

FIG. 14 illustrates an exemplary embodiment of a tool 502 that can be used for implanting a bone screw or anchor, which includes at least certain general features as described elsewhere herein, and additionally including a torsion spring that is used to cause rotation of an inner rotating shaft and thereby drive a helical anchor into soft tissue. Tool 502 includes a torsion spring housing 504, a proximal end 512 having a handle 518, an actuator 514, and a shaft 520 that includes a rotating shaft that can be rotated by a torsion spring 530 that is located at a proximal end of the device. The actuator 514 can be used both to unlock the device for actuation and to allow a coil to drive the anchor as a plunger 516 is pulled forward. In this way, a desired torque will drive a helical anchor and control a number of revolutions of the rotating shaft to an amount that drives the helical anchor a desired depth, e.g., from 2 to 10 rotations, such as from 3 to 4 rotations, optionally 3.5 rotations.

Figure 15:
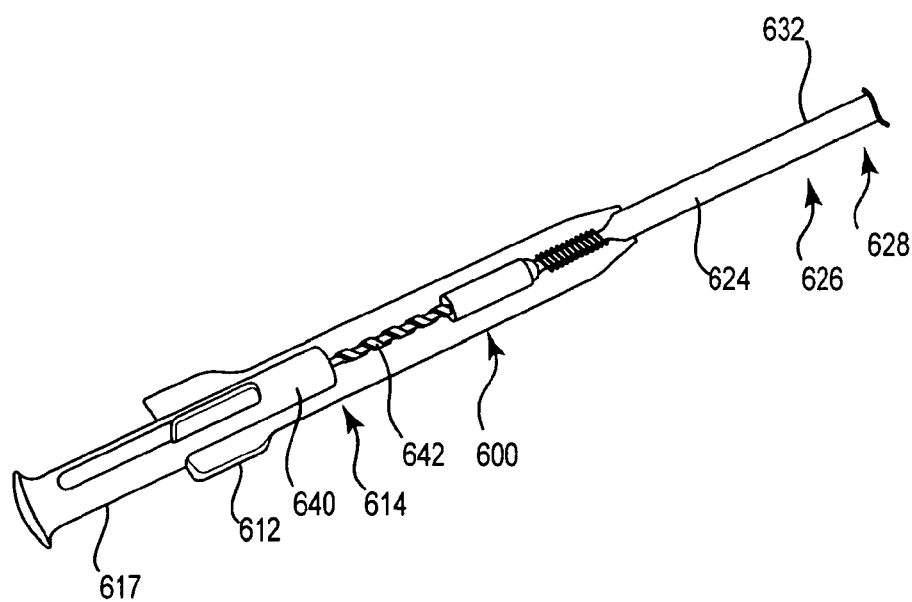
FIG. 15 is a perspective view of an embodiment of an anchor insertion tool, in accordance with the invention.

Another embodiment of a driver 600 is illustrated in FIG. 15, which includes proximal end a 612, which includes a handle 614 and a movable actuator or "plunger" 617. Proximal end 612 engages a proximal end of a shaft 624, which extends to a distal end 626 and a tip 628. A helical anchor can engage with tip 628. The length of shaft 624 is sufficient to allow a user to grasp and manipulate the proximal end 612 to thereby place distal shaft end 626, tip 628, and helical anchor at a location of a posterior pelvic region (e.g., to place the distal shaft end at a location for placing the helical anchor at a component of sacral anatomy). Shaft 624 includes an outer shaft 632 and an inner rotating shaft. When actuator 617 is moved in a proximal direction relative to handle 614, a barrel 640 moves distally along a threaded portion 642, producing rotational movement of the rotating inner shaft about its rotational (longitudinal) axis and consequently causing the helical anchor to rotate about the same axis (which can coincide with the longitudinal axis of the helical anchor).

A driver 600, as illustrated, can provide manually driven motion for rotationally inserting a helical anchor into a desired location. The driver can convert axial linear motion of actuator 617 into rotational motion of shaft, which can be useful for screwing a helical fixation element into soft tissue. The distal end can optionally provide for shielding the helical anchor at the distal end (tip) during delivery, to ensure sterility. The driver can also optionally be equipped with a mechanism to easily re-load and deliver additional helical anchors. The driver can also optionally include a mechanism for temporarily locking the device once delivery (screwing, rotational movement) is completed so as to prevent the user from unscrewing the helical anchor from an installed location.

Figure 16:
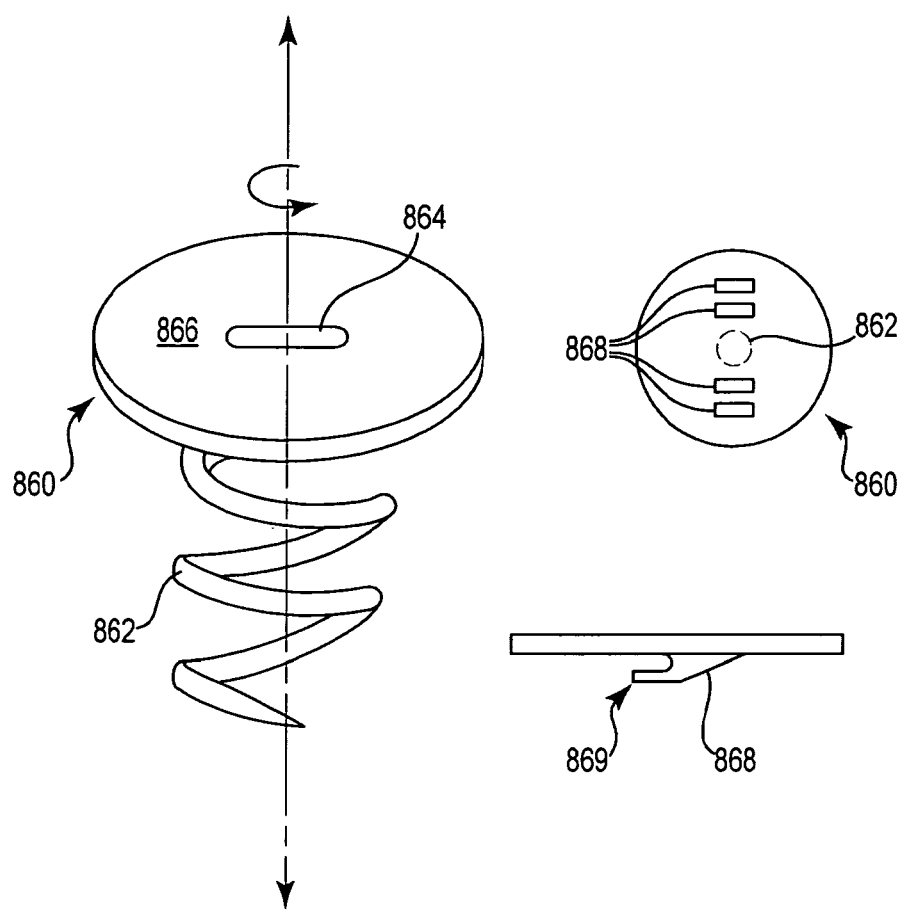
FIG. 16 is a top perspective view of an anchor member that can be used with anchor insertion tools of the invention.

Tools as described can be useful to place a helical anchor, which may be any anchor having a helical feature that can be driven into tissue by rotation around an axis, to thereafter support an implant. FIG. 16 shows an example of a helical anchor 860 incorporating a screw (e.g., a molded screw) that can be inserted by rotation into tissue in one direction, and includes an anti-rotation feature to prevent reverse rotation. The anti-rotation features lock on a mesh implant (not shown), preventing the anchor from reverse rotation that would allow the anchor to move out of the tissue. In specific, anchor 860 includes screw head 866, a slot 864 to allow rotation, a helical screw (or "coil") 862, and at least one anti-rotation hook or barb 868 on the underside of screw head 866. By rotating anchor 860 in a direction to drive screw 862 into tissue, hooks or barbs 868 are brought to contact a surface of the tissue or an implant material held to the tissue by the anchor. Barbs 868 can be any counter-rotation-preventive structure located on the underside of screw head 866 to prevent counter-rotation, and may in preferred embodiments include a tapered profile with a sharp or enlarged trailing edge 869 that inhibits movement in a direction that is the reverse of the direction used to drive screw 862 into tissue.

Figure 17:
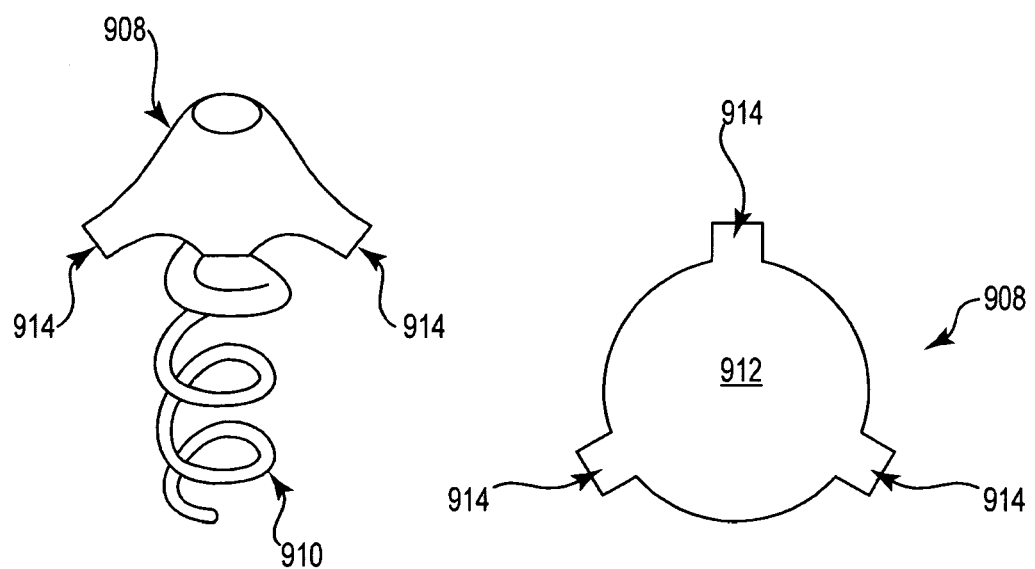
FIG. 17 includes a side view and a top view of an anchor member that can be used with anchor insertion tools of the invention.

An embodiment of another anchor that can be used in accordance with the drivers of the invention is illustrated in FIG. 17. A helical fixation element (anchor) 908 can be used for fixation of a helical screw or coil portion 910 and cap 912 to tissue prior to attaching the implant (e.g., mesh). Anchor 908 can further provide for a manner of double checking by the operator of a fixation strength prior to attaching an implant, along with a greater degree of coil location control in tissue (when using more than one coil) due to the number of pores in the mesh. In addition, anchor 908 can be used for electrocautery because the driver is on the outside of the coil portion 910 and can make contact, with coil portion 910, and the prong feature 914 of the cap 912 can prevent coil portion 910 from backing out by locking onto the mesh.

The placement, depth, and degree of strength of placement of anchor 908 can be tested and if desired, the anchor 908 can be removed and repositioned to another location. After the integrity and position of anchor 908 is satisfactory, an aperture of an implant (e.g., mesh) can be placed over cap 912 to secure the implant to cap 912, anchor 908, and the tissue. Due to the configuration and functionality of cap 912, cap 912 can be made smaller or larger than coil portion 910. Regardless, the cap can secure to an implant through an aperture. In addition, the operator can see the engagement of anchor 908 with tissue, with greater ease, because the amount of material in the working area when completing the procedure is reduced by not including the implant. Various materials, such as stainless steel, polyurethane, polycarbonate, polypropylene and like materials can be used to produce the structures or components thereof.

The various systems, apparatus, and methods detailed herein are envisioned for use with known implant and repair systems or improvements thereof (e.g., for male and female), including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, WO 2009/017680, and U.S. Patent Publication Nos. 2002/151762, 2010/0174134, 2010/0298630, 2002/0028980, 2006/0069301, and 2002/147382, and International Application number PCT/US10/62577 (filed Dec. 30, 2010). Accordingly, the above-identified disclosures are fully incorporated herein by reference in their entirety.

An implant for placement by use of the described tools, methods, and helical anchors, and their various components, structures, features, materials and methods may have a number of suitable configurations as shown and described in the previously-incorporated references or as described herein or elsewhere. Various methods and tools for introducing, deploying, anchoring, and manipulating implants to treat incontinence, prolapse, or another pelvic condition, as disclosed in the previously-incorporated references are envisioned for possible adapted use with devices and methods described herein.

An implant for use as described herein can include any structural features useful for a desired treatment, including any desired size, shape, and optional features such as adjustability. Any of these features may be previously known, or described in documents incorporated herein, or as described herein, for any particular implant and method. An implant that includes or is otherwise secured by an anchor as described, using a tool ("driver") as described, might be useful to treat any type of pelvic condition in a male or a female patient; as a single and non-limiting example, an implant that includes or uses a helical anchor can be used in an abdominal, laparoscopic, or transvaginal SCP procedure to provide support to a vaginal cuff, through an implant that includes the anchor, the anchor being attached at a region of sacral anatomy such as a sacral ligament (e.g., anterior longitudinal ligament, a.k.a. the "anterior ligament" or "longitudinal ligament").

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A tool for driving a helical anchor into a target location, the tool comprising:
    a proximal portion and a distal portion, the proximal portion comprising a handle and an actuator;
    a shaft extending distally from the proximal portion, the shaft comprising an outer shaft and an inner rotating shaft that is at least partially concentrically positioned within the outer shaft, the shaft comprising a length that facilitates accessing a location of a posterior pelvic region; and
    a cylindrical barrel moveable along a longitudinal axis of the shaft, wherein the cylindrical barrel comprises a notch that is selectively engageable and disengageable with the actuator,
    wherein the inner rotating shaft is actuated by movement of the actuator in a proximal direction relative to the handle.

2. The tool of claim 1, wherein the target location comprises tissue.

3. The tool of claim 1, wherein the target location comprises bone.

4. The tool according to claim 1, wherein the cylindrical barrel is operatively engaged with the outer shaft.

5. The tool of claim 4, wherein the cylindrical barrel comprises an outer surface and the notch extends inwardly from the outer surface toward a longitudinal axis of the barrel.

6. The tool according to claim 5, wherein the actuator comprises an extendable and retractable latch that is engageable and disengageable from the notch of the barrel.

7. The tool according to claim 6, wherein the actuator further comprises a trigger.

8. The tool of claim 1 in combination with a helical anchor, wherein movement of the actuator toward the handle actuates the inner rotating shaft, and wherein a single stroke movement of the actuator produces rotational movement of the inner rotating shaft sufficient to rotate the helical anchor a predetermined number of rotations to cause the helical anchor to be driven into a target location.

9. The tool of claim 1 in combination with a helical anchor, wherein movement of the actuator toward the handle actuates the inner rotating shaft, and wherein multiple stroke movement of the actuator produces rotational movement of the inner rotating shaft sufficient to rotate the helical anchor a predetermined number of rotations to cause the helical anchor to be driven into a target location.

10. The tool of claim 1 in combination with a helical anchor, wherein the helical anchor comprises a head comprising a surface and a helical portion extending from the surface.

11. The combination of claim 10 wherein the helical portion comprises a longitudinal axis, a length along the longitudinal axis, and a diameter perpendicular to the longitudinal axis, and wherein the head comprises a diameter perpendicular to the longitudinal axis, and wherein the diameter of the helical portion is less than the diameter of the head.

12. The combination of claim 10 wherein the head comprises an underside facing the helical portion, the underside comprising an extension adapted to engage tissue and prevent reverse rotation of the helical anchor when the helical anchor is installed at the tissue.

13. The combination of claim 10 wherein the head comprises a perimeter, the perimeter comprising one or more extensions adapted to engage tissue and prevent reverse rotation of the helical anchor when the helical anchor is installed at the tissue.

14. The combination of claim 10 further comprising a mesh implant.

15. The combination of claim 14 wherein the mesh implant comprises an opening that is capable of being passed over the head of the anchor to secure the mesh to the helical anchor.

16. A method of performing a sacral colpopexy, the method comprising:
   providing a tool according to claim 1;
   providing an implant comprising an anterior end and a posterior end;
   placing the anterior end of the implant in contact with vaginal tissue in a region of a vaginal apex;
   placing the posterior end of the implant at a component of sacral anatomy; and
   driving a helical anchor into the target location with the tool to secure the posterior end of the implant at the component of sacral anatomy.

17. The method of claim 16, wherein the posterior end of the implant comprises the helical anchor and the component of sacral anatomy comprises an anterior longitudinal ligament.

18. A tool for driving a helical anchor into a target location, the tool comprising:
   a proximal portion and a distal portion, the proximal portion comprising a handle and an actuator;
   a shaft extending distally from the proximal portion, the shaft comprising an outer shaft and an inner rotating shaft that is at least partially concentrically positioned within the outer shaft, the shaft comprising a length that facilitates accessing a location of a posterior pelvic region; and
   a cylindrical barrel operatively engaged with the outer shaft and wherein the cylindrical barrel comprises an outer surface and a notch extending inwardly from the outer surface toward a longitudinal axis of the barrel;
   wherein the inner rotating shaft is actuated by movement of the actuator in a predetermined motion; and
   wherein the actuator comprises an extendable and retractable latch that is engageable and disengageable from the notch of the barrel.

19. The tool according to claim 18, wherein the actuator further comprises a trigger.

20. A method of performing a sacral colpopexy, the method comprising:
   providing a tool according to claim 18;
   providing an implant comprising an anterior end and a posterior end;
   placing the anterior end of the implant in contact with vaginal tissue in a region of a vaginal apex;
   placing the posterior end of the implant at a component of sacral anatomy; and
   driving a helical anchor into the target location with the tool to secure the posterior end of the implant at the component of sacral anatomy.

* * * * *